US005728401A

United States Patent [19]
Ahmed et al.

[11] Patent Number: 5,728,401
[45] Date of Patent: Mar. 17, 1998

[54] EFFERVESCENT RANITIDINE FORMULATIONS

[75] Inventors: Farhan Ahmed; Chetan Rajsharad, both of New Delhi; Himadri Sen, Haryana, all of India

[73] Assignee: Ranbaxy Laboratories, Ltd., New Delhi, India

[21] Appl. No.: 837,488

[22] Filed: Apr. 16, 1997

[51] Int. Cl.⁶ ........................................ A61K 9/46
[52] U.S. Cl. .................. 424/466; 424/465; 424/499
[58] Field of Search ........................ 424/466, 499, 424/465

[56] References Cited

U.S. PATENT DOCUMENTS

| | | |
|---|---|---|
| 4,585,790 | 4/1986 | Padfield et al. |
| 4,704,269 | 11/1987 | Korab .................................. 424/44 |
| 4,824,664 | 4/1989 | Tarral et al. |
| 4,942,039 | 7/1990 | Duvall et al. ......................... 424/466 |
| 5,064,656 | 11/1991 | Gergely et al. ....................... 424/463 |
| 5,102,665 | 4/1992 | Schaeffer . |
| 5,164,192 | 11/1992 | Louwes ................................ 424/466 |
| 5,415,870 | 5/1995 | Gergely et al. . |
| 5,424,075 | 6/1995 | Daher et al. . |

Primary Examiner—Thurman K. Page
Assistant Examiner—Lakshmi Channavajjala
Attorney, Agent, or Firm—Meltzer, Lippe, Goldstein et al.

[57] ABSTRACT

An effervescent pharmaceutical composition for oral use in the treatment of a condition mediated through histamine $H_2$ receptors contains a therapeutically effective amount of ranitidine or a physiologically acceptable salt thereof, about 25–70% by weight of disodium citrate, and about 20–50% by weight of sodium bicarbonate. Optionally, the effervescent composition may also include about 0.5–25% by weight of an edible organic acid such as fumaric acid. Preferably, the effervescent composition is in the form of a tablet. Additional excipients for the effervescent composition include about 2–10% by weight of glycine, a flavoring agent, a sweetening agent, a binding agent, and/or a lubricant.

29 Claims, No Drawings of disodium citrate and sodium bicarbonate, in the indicated amounts, it is believed that a significant portion of the disodium citrate in the formulation will react with sodium bicarbonate during dissolution of the tablet in water to form trisodium citrate. It has been observed in cimetidine efferves-

EFFERVESCENT RANITIDINE FORMULATIONS

BACKGROUND OF THE INVENTION

The present invention relates to effervescent ranitidine formulations. More particularly, the present invention relates to a composition, preferably a tablet, containing ranitidine base or ranitidine hydrochloride as the active ingredient, and an effervescent couple. The effervescent couple comprises disodium citrate and sodium bicarbonate. Upon placing the ranitidine tablet in water, a pleasantly flavored ranitidine-containing liquid is produced which is suitable for oral administration.

Ranitidine, chemically identified as N-[2-[[[5-(dimethylamino)methyl-2-furanyl]methyl]thio]ethyl]-N'-methyl-2-nitro-1,1-ethenediamine is a competitive reversible inhibitor of the action of histamine at $H_2$-receptors. Ranitidine inhibits both day time and nocturnal basal gastric acid secretions, as well as gastric acid secretions stimulated by food, betazola, and pentagastrin. A 150 mg dose of ranitidine inhibits basal acid secretion by 95% for up to four hours, nocturnal acid secretion by 92% for up to thirteen hours, and betazole, stimulated secretion by 97% for up to three hours. Additionally, pepsin output is reduced in proportion to the decrease in volume of gastric juice. Ranitidine is well absorbed after oral administration and remains in the effective range of 36–94 mg/ml for about twelve hours.

Ranitidine is generally available as its physiologically acceptable salt, more specifically, Form 2 ranitidine hydrochloride, as uncoated or film coated tablets for oral use. It is also available in the form of a syrup for oral administration. The syrup contains flavorants which mask the unpleasant taste of ranitidine.

It is desirable to make ranitidine available as an effervescent composition, particularly as an effervescent tablet since such a tablet provides many of the advantages of both a tablet and a liquid formulation. Among the benefits of an effervescent tablet are the following:

a. A palatable liquid dosage form is provided as an alternative to the solid form.
b. An effervescent formulation is useful for patients who need or prefer to take a liquid formulation, particularly elderly patients and those with dysphagia.
c. Since a liquid formulation is more palatable than solid dosage form, it is more acceptable to patients and results in greater adherence to the prescribed therapy regimen.
d. A liquid containing the effervescent formulation provides an immediate and sustained increase in intragastric pH. The effervescent mixture also provides an immediate transient increase in pH of the oesophagus and stomach. This buffering action provides immediate relief, yet there is no rebound in acid secretion because ranitidine blocks the $H_2$-receptors. This property is especially useful in dyspepsia and NSAID induced gastritis.
e. An effervescent formulation provides the stability of a dry formulation, yet is easily convertible into liquid form.

In general, an effervescent composition contains, in addition to the active ingredient, an effervescent couple comprising a physiologically acceptable acid source (such as citric acid, tartaric acid, or fumaric acid), and a source of carbon dioxide (such as sodium/potassium carbonate/bicarbonate).

U.S. Pat. No. 4,824,664 (Tarral et al.) discloses an effervescent pharmaceutical composition comprising the histamine $H_2$-antagonist cimetidine and an effervescent couple. To prepare the effervescent couple, citric acid is partially neutralized during processing by reacting with an alkali metal carbonate or bicarbonate. The reaction is controlled so that only 24–54% carbon dioxide is released. The effervescent couple contains a mixture of monosodium and disodium citrate within a specified ratio, and an alkali metal carbonate or bicarbonate.

U.S. Pat. No. 5,102,665 (Schaeffer) discloses an effervescent pharmaceutical composition containing ranitidine or a physiologically acceptable salt thereof, a monoalkali metal citrate, and an alkali metal or alkaline earth metal carbonate or bicarbonate. According to that patent, the monoalkali citrate, usually monosodium citrate, is the sole source of acid.

U.S. Pat. No. 5,415,870 (Gergely) discloses an effervescent tablet containing a pharmaceutically active substance and an effervescent system comprising at least one edible organic acid, at least one alkali metal carbonate or bicarbonate, and at least one solid, edible alkali metal salt of the acid. Furthermore, carrier crystals of the organic acid are covered with a first layer of a different organic acid and a second layer of a salt of at least one of the two organic acids. Ranitidine and cimetidine are disclosed as possible active ingredients.

U.S. Pat. No. 5,424,075 (Daher et al.) discloses a swallowable tablet containing an effective amount of a therapeutic drug, such as ranitidine or cimetidine, and 0.250 to 1.0 grams per tablet of a salt of an edible organic acid, such as trisodium citrate. The tablet may also contain a carbonate or bicarbonate, such as sodium bicarbonate. The tablet of this patent is intended to be swallowed and to disintegrate in vivo. The patent is not directed to an effervescent composition or an effervescent tablet which produce a liquid for oral administration upon being placed in water.

SUMMARY AND DETAILED DESCRIPTION OF THE INVENTION

In accordance with the present invention, an effervescent composition for oral use in the treatment of a condition mediated through histamine $H_2$ receptors is provided comprising a therapeutically effective amount of ranitidine or a physiologically acceptable salt thereof, about 25% to 70% by weight of disodium citrate, and about 20% to 50% by weight of sodium bicarbonate. Optionally, the effervescent composition may also contain about 0.5 to about 25% by weight of fumaric acid. The effervescent composition may be formulated as a powder, as granules, or as a tablet by conventional techniques. Upon placing the effervescent composition in water, a palatable liquid suitable for oral administration to a patient is obtained.

The active ingredient may be either ranitidine in its free base form, or its physiologically acceptable salts, such as ranitidine hydrochloride (Form 1 or Form 2). Desirably, the effervescent composition contains a dose of 50 to 600 mg of ranitidine per unit, wherein the dose of ranitidine is expressed as the equivalent weight of the free base in said effervescent composition.

Disodium citrate is the preferred acid source in the effervescent composition in an amount ranging from about 25% to about 70%, preferably 40 to 70%, by weight of the effervescent composition. Pharmaceutical grade disodium citrate is widely available and has a recognized monograph in the British Pharmacopoeia. Monoalkali metal and trialkali metal citrates are avoided in the effervescent couple of the present invention.

The carbon dioxide source in the inventive effervescent composition is sodium bicarbonate. Sodium bicarbonate is compatible with disodium citrate.

In a preferred embodiment of the invention, the effervescent composition further contains about 2–10% w/w of glycine. Glycine is an amino acid which, in combination with disodium citrate, results in faster effervescence of the composition, especially when it is produced in tablet form. When disodium citrate is present in an effervescent tablet in accordance with the present Invention, the tablet becomes engulfed by bubbles of carbon dioxide, thus lowering the effective density of the tablet. This causes the tablet to float to the surface of the liquid and reduces the surface area in contact with the liquid. Thus, the overall effervescence time of the tablet may be increased to unacceptable levels. Surprisingly, it has been found that when glycine is present in the effervescent tablet, this phenomenon is prevented and the tablet remains below the surface of the liquid at all times. The contact area of the effervescent tablet is therefore maximized and the time for complete effervescence is reduced.

For example, it has been observed that the disintegration time for ranitidine effervescent tablets made in accordance with the present invention but without glycine is 4–6 minutes. However, when glycine in amounts of 2–10% w/w are incorporated into the tablets, disintegration times of 100–150 seconds are observed.

In place of glycine, other amino acids, such as sarcosine, alanine, taurine, and glutamic acid, alone or in combination, may also be used. However, glycine is preferred because of its superior taste-masking capability.

In addition to the ingredients mentioned above, other excipients may also be incorporated into the effervescent composition. For example, a conventional binding agent, such as polyvinylpyrrolidone (PVP) in an amount of about 1–4% w/w, or hydroxypropyl methyl cellulose (HPMC) of low viscosity in an amount of about 0.2 to 3.0% w/w may also be included. Conventional sweetening agents, such as sodium saccharin, aspartame, or sodium cyclamate may also be included in an amount of about 0.25–1.5% w/w. Conventional flavoring agents, such as peppermint, cola, cherry, apricot, lemon-lime or combinations thereof may be included in an amount of about 0.5–2.0% w/w. In addition, a conventional lubricant, such as simethicone (0.05–0.5% w/w), or sodium benzoate (0.5–4.0% w/w), polyethylene glycols (0.1–5.0% w/w), or their combinations may be included.

The effervescent composition is prepared by mixing disodium citrate, sodium bicarbonate, glycine, and any other excipients. The mixture thus obtained is formed into granules by conventional granulating techniques using ethyl alcohol, isopropyl alcohol, and water, or combinations thereof, as the granulating fluid. The granules are dried and then blended with ranitidine base or its hydrochloride salt. The blended granules may be used as such or may be formed into tablets by conventional tabletting techniques.

It is important that the final product have a high degree of stability. Ranitidine and its salt are unstable in the presence of moisture and elevated temperature. When ranitidine is granulated along with the other excipients, and then subjected to a drying cycle, it is likely to give stability problems. Therefore, in accordance with the present invention, effervescent granules comprising disodium citrate, sodium bicarbonate, a binding agent and one or more of the other excipients, such as a sweetener or glycine, are first formed into effervescent granules and then dried. These granules have a moisture content of less than 0.25% w/w. The granules are then blended with ranitidine and the remaining excipients, and afterwards compressed into tablets, if desired. This process provides excellent stability, since ranitidine is not exposed to the rigors of moisture and heat during granulation and drying.

The final product is then packed in aluminum foil to prevent exposure to atmospheric humidity and temperature. This ensures that the product will remain stable until utilized by the consumer.

In place of disodium citrate as the sole acid source, the acid source may comprise disodium citrate in combination with a weak edible organic acid, such as fumaric acid. The fumaric acid may be present in the effervescent composition in an amount ranging from about 0.5% to about 25%, preferably from about 3% to about 15% by weight, of the weight of the effervescent composition. Alternatively, the fumaric acid may be present in an amount ranging from about 5% to about 50% by weight of the weight of the disodium citrate. The fumaric acid is added to the composition and granulated with inactive ingredients such that they form an intragranular component. The active ingredient along with any remaining inactive ingredients are then blended with the granulated component to form the effervescent composition which may then be tabletted.

The present invention will now be illustrated by the following examples, wherein ranitidine hydrochloride is the active ingredient in the effervescent compositions of Examples 1–6, while ranitidine free base is the active ingredient in the effervescent composition of Example 7.

EXAMPLE 1

| Ingredients | mg/3.6 gm tablet |
| --- | --- |
| Disodium citrate | 2148.0 |
| Sodium Bicarbonate | 1100.0 |
| Sodium Saccharin | 30.0 |
| Polyvinylpyrrolidone | 72.0 |
| Ranitidine Hydrochloride* | 167.5 |
| Peppermint flavor | 36.0 |
| Simethicone | 4.5 |
| Sodium Benzoate | 42.0 |
| Ethyl alcohol for granulation | q.s. |

*equivalent to 150 mg free base

Disodium citrate, sodium bicarbonate, and sodium saccharin, in the amounts shown above, were mixed together and granulated with polyvinylpyrrolidone in ethyl alcohol. The granules were dried in a tray drier or in a fluid bed drier. Ranitidine hydrochloride was thoroughly mixed with the dried granules. The resulting material is further mixed with peppermint flavor, simethicone, and sodium benzoate as indicated above. The granulated blend is then compressed into 150 mg per unit dose tablets using 25 mm toolings.

EXAMPLE 2

| Ingredients | mg/3.6 gm tablet |
| --- | --- |
| Disodium citrate | 1744.0 |
| Sodium Bicarbonate | 1150.0 |
| Sodium Saccharin | 30.0 |
| Polyvinylpyrrolidone | 72.0 |
| Ranitidine Hydrochloride* | 167.5 |
| Glycine | 360.0 |
| Peppermint flavor | 36.0 |
| Simethicone | 4.5 |
| Sodium Benzoate | 36.0 |
| Ethyl alcohol for granulation | q.s. |

*equivalent to 150 mg free base

Tablets with the ingredients shown above were prepared in the same manner as in Example 1. Glycine was added after the addition of ranitidine hydrochloride to the effervescent granules. The other excipients were added after the addition of glycine.

In preparing the granules, water and isopropyl alcohol were used as the granulating fluid in place of the ethyl alcohol of Example 1. Various combinations of the three solvents may also be used. In such cases, polyvinylpyrrolidone is dry mixed with disodium citrate, sodium bicarbonate, and sodium saccharin. The mixture is then granulated in the indicated solvent system.

EXAMPLE 3

| Ingredients | mg/3.6 gm tablet |
| --- | --- |
| Disodium citrate | 2053.0 |
| Sodium Bicarbonate | 1050.0 |
| Sodium Saccharin | 30.0 |
| Polyvinylpyrrolidone | 72.0 |
| Rantidine Hydrochloride* | 167.5 |
| Glycine | 145.0 |
| Peppermint flavor | 36.0 |
| Simethicone | 4.5 |
| Sodium Benzoate | 42.0 |
| Ethyl alcohol for granulation | q.s. |

*equivalent to 150 mg free base

Effervescent tablets containing ranitidine with the ingredients indicated above were prepared as described in connection with Example 2.

EXAMPLE 4

| Ingredients | mg/3.6 gm tablet |
| --- | --- |
| Disodium citrate | 2053.0 |
| Sodium Bicarbonate | 1050.0 |
| Sodium Saccharin | 30.0 |
| Polyvinylpyrrolidone | 72.0 |
| Rantidine Hydrochloride* | 167.5 |
| Glycine | 145.0 |
| Flavor powder** | 36.0 |
| Simethicone | 4.5 |
| Sodium Benzoate | 42.0 |
| Ethyl alcohol for granulation | q.s. |

*equivalent to 150 mg free base
**each of the following flavor powders were used separately: cola, cherry, apricot, lemon-lime Effervescent tablets containing ranitidine with the ingredients indicated above were prepared as described in connection with Example 3.

EXAMPLE 5

| Ingredients | mg/3.6 gm tablet |
| --- | --- |
| Disodium citrate | 2080.0 |
| Sodium Bicarbonate | 1070.0 |
| Sodium Saccharin | 30.0 |
| Hydroxypropyl Methyl Cellulose | 25.0 |
| Rantidine Hydrochloride* | 167.5 |
| Glycine | 145.0 |
| Peppermint flavor | 36.0 |
| Simethicone | 4.5 |
| Sodium Benzoate | 42.0 |
| Ethyl alcohol for granulation | q.s. |

*equivalent to 150 mg free base

Disodium citrate, sodium bicarbonate, sodium saccharin and hydroxypropyl methyl cellulose in the amounts shown above were mixed together and granulated using ethyl alcohol. The granules were dried. Ranitidine hydrochloride was thoroughly mixed with the dried granules. The resulting material was further mixed with glycine and with the remainder of the excipients. The granulated blend was then compressed into tablets using 25 mm tooling.

In Examples 1–5 above, in place of sodium saccharin, sodium cyclamate (15–150 mg) or aspartame (15–75 mg), or combinations thereof may be used as the sweetener.

EXAMPLE 6

| Ingredients | mg/3.6 gm tablet |
| --- | --- |
| Disodium citrate | 1659.0 |
| Fumaric acid | 450.0 |
| Sodium bicarbonate | 1000.0 |
| Sodium saccharin | 30.0 |
| Polyvinylpyrrolidone | 72.0 |
| Rantidine hydrochloride* | 167.50 |
| Glycine | 145.0 |
| Peppermint flavor | 36.0 |
| Simethicone | 4.5 |
| Sodium benzoate | 36.0 |
| Ethyl alcohol for granulation | Q.S. |

*equivalent to 150 mg free base

Disodium citrate, fumaric acid, sodium bicarbonate, sodium saccharin, and polyvinyl pyrrolidone in the amounts shown above were mixed together and granulated using ethyl alcohol. The granules were dried. These granules were mixed with the rest of the ingredients and were compressed into tablets using 25 mm tooling.

EXAMPLE 7

| Ingredients | mg/3.6 gm tablet |
| --- | --- |
| Disodium citrate | 2092.0 |
| Sodium Bicarbonate | 1000.0 |
| Sodium Saccharin | 30.0 |
| Polyvinylpyrrolidone | 72.0 |
| Rantidine (free base) | 150.0 |
| Glycine | 145.0 |
| Peppermint flavor | 36.0 |
| Simethicone | 5.0 |
| Sodium Benzoate | 70.0 |
| Ethyl alcohol for granulation | q.s. |

Effervescent tablets containing ranitidine free base and the other ingredients indicated above were prepared. The method used to prepare such tablets was the same as described in connection with Example 2.

While the invention has been described by reference to specific embodiments, this was for purposes of illustration only. Numerous alternative embodiments will be apparent to those skilled in the art and are considered to be part of the invention.

What is claimed is:

1. An effervescent pharmaceutical composition for oral use in the treatment of a condition mediated through histamine $H_2$ receptors, comprising a therapeutically effective mount of ranitidine or a physiologically acceptable salt thereof, about 25% to about 70% by weight of disodium citrate, about 2–10% by weight of an amino acid, and about 20% to about 50% by weight of sodium bicarbonate, and optionally also comprising about 0.5% to about 25% by weight of an edible organic acid.

2. The pharmaceutical composition of claim 1 which contains a therapeutically effective amount of ranitidine free base.

3. The pharmaceutical composition of claim 1 which contains a therapeutically effective amount of ranitidine hydrochloride.

4. The pharmaceutical composition of claim 1 which contains 50–600 mg per unit dose of ranitidine or its physiological salt expressed as the equivalent of ranitidine free base.

5. The pharmaceutical composition of claim 1 which comprises about 40–70% by weight of disodium citrate.

6. The pharmaceutical composition of claim 1 wherein said amino acid comprises glycine.

7. The pharmaceutical composition of claim 1 wherein said amino acid is glycine, sarcosine, alanine, taurine, glutamic acid, or a combination thereof.

8. The pharmaceutical composition of claim 1 further comprising at least one additional excipient.

9. The pharmaceutical composition of claim 8 wherein said additional excipient comprises a flavoring agent.

10. The pharmaceutical composition of claim 8 wherein said additional excipient comprises a sweetening agent.

11. The pharmaceutical composition of claim 10 wherein said sweetening agent is sodium saccharin, aspartame, sodium cyclamate, or combinations thereof.

12. The pharmaceutical composition of claim 8 wherein said additional excipient comprises a binding agent.

13. The pharmaceutical composition of claim 12 wherein said binding agent is polyvinylpyrrolidone or hyroxypropyl methyl cellulose.

14. The pharmaceutical composition of claim 8 wherein said additional excipient is a lubricant.

15. The pharmaceutical composition of claim 14 wherein said lubricant is simethicone, sodium benzoate, or mixtures thereof.

16. The pharmaceutical composition of claim 1 in the form of a tablet.

17. The pharmaceutical composition of claim 1 in the form of granules or a powder.

18. The pharmaceutical composition of claim 1 wherein said edible organic acid is fumaric acid.

19. A process for making an effervescent composition comprising mixing together disodium citrate and sodium bicarbonate in a solvent system, forming said mixture of disodium citrate and sodium bicarbonate into granules, drying said granules to remove any solvents in said solvent system, and mixing said granules with ranitidine or a physiologically acceptable salt thereof, wherein said disodium citrate comprises about 25 to about 70% by weight of said composition, and said sodium bicarbonate comprises about 20% to about 50% by weight of said composition, said process further comprising adding about 2–10% by weight of an amino acid to said composition.

20. The process of claim 19, further comprising compressing said mixture of disodium citrate, sodium bicarbonate, and ranitidine into a tablet.

21. The process of claim 19, wherein said amino acid comprises glycine.

22. The process of claim 19, further comprising adding at least one additional excipient to said mixture.

23. The process of claim 22, wherein said additional excipient is a flavoring agent.

24. The process of claim 22, wherein said additional excipient is a sweetening agent.

25. The process of claim 22, wherein said additional excipient is a binding agent.

26. The process of claim 22, wherein said additional excipient is a lubricant.

27. The process of claim 19 wherein said amino acid is glycine, sarcosine, alanine, taurine, glutamic acid, or combinations thereof.

28. The process of claim 19 further comprising mixing an edible organic acid with said disodium citrate end sodium bicarbonate in said solvent system, wherein said edible organic acid comprises about 0.5% to about 25% by weight of said composition.

29. The process of claim 28 wherein said edible organic acid is fumaric acid.

* * * * *